United States Patent [19]

Imaizumi et al.

[11] Patent Number: 5,754,921
[45] Date of Patent: May 19, 1998

[54] COPIER HAVING A DENSITY DETECTOR WITH FLUORESCENT-DYE-COATED REFLECTING PLATE

[75] Inventors: Kazuaki Imaizumi; Yukio Takemura, both of Kawasaki, Japan

[73] Assignee: Canon Kabushiki Kaisha, Tokyo, Japan

[21] Appl. No.: 798,175

[22] Filed: Feb. 10, 1997

[30] Foreign Application Priority Data

Feb. 15, 1996 [JP] Japan .................. 8-054273

[51] Int. Cl.⁶ ...................................... G03G 21/00
[52] U.S. Cl. ............................................. 399/52
[58] Field of Search ...................... 399/73, 74, 45, 399/52, 17

[56] References Cited

U.S. PATENT DOCUMENTS 5,325,153  6/1994  Mitsuse et al. ................. 399/74

Primary Examiner—S. Lee
Attorney, Agent, or Firm—Fitzpatrick, Cella, Harper & Scinto

[57] ABSTRACT

An original density detecting apparatus includes a projector-receiver including a light projector and a light receiver, and a reflecting member including a fluorescent reflecting plate a surface of which on the projector-receiver side is a coating of a fluorescent dye. An image forming apparatus includes an illuminating device for illuminating an original, an image reader for forming an image of the original on a photosensitive medium, and the original density detecting apparatus as described above.

9 Claims, 4 Drawing Sheets

COPIER HAVING A DENSITY DETECTOR WITH FLUORESCENT-DYE-COATED REFLECTING PLATE

BACKGROUND OF THE INVENTION

1. Field of the Invention

The present invention relates to an original density detecting apparatus (original reflectivity detecting apparatus) and, more particularly, the invention concerns an original density detecting apparatus mounted in a copier (image forming apparatus) or the like equipped with an automatic original supplying apparatus and arranged in such a manner that when one of originals (measured objects) stacked on an original tray is moved to the main body of copier to read image information of the original, a reflection density (reflectivity) of the original is detected accurately in a measurement region in an original conveyance path (sheet path section) through which the original moves at high speed.

2. Related Background Art

FIG. 1 is a schematic drawing of the major part of a copier (image forming apparatus) having an automatic original supplying apparatus provided with a conventional original density detecting apparatus.

In the drawing, when a copy start switch (not shown) of the copier main body 120 is turned on, a detection sensor (original presence/absence detection sensor) 131 first detects presence or absence of original 102 mounted in a stack on the original tray 101, an output signal from the detection sensor 131 is put into the copier main body 120, and then calibration of original density detecting apparatus 200 is carried out.

FIG. 2 is a partially enlarged view of this original density detecting apparatus 200. In the drawing, a light source (LEDs) 51 as a light projecting device (projector) for detection of original density emits light beams toward a white plate 53, which is a metal plate covered by a white coating and the reflectivity of which is preliminarily known; reflected light from the white plate 53 is received by a photoelectric sensor (original density detection sensor) 55, for example, of SBC or the like, as a light receiving device (receiver) through an imaging lens 54; the photoelectric sensor 55 converts the received light to an electric value (electric signal value) v1 proportional to a quantity of the received light by photoelectric conversion; and the electric value is stored in a memory (not shown). The electric signal value v1 at this time is used as a reference of original density.

An example of the material for the white coating of the white plate 53 is Yupo FP#110 (from Oji Yuka Goseishi Hanbai Kabushiki Kaisha).

Since the light projecting device (light source) 51 and the light receiving device (photoelectric sensor) 55 can be disposed closely, these elements are placed on a same printed board in the drawing. These light projecting device 51 and light receiving device 55 will be referred to together as projector-receiver 61.

The projector-receiver 61 and the aforementioned white plate 53 need to be placed carefully in the following respects.

The original 102, conveyed at high speed, passes in the original conveyance path (sheet path section) 118 with some dispersion of position. If this original 102 should touch a part of the white plate 53 or the projector-receiver 61, they could scratch the original 102 to damage the original 102 or an original jam could occur. In order to avoid such accidents, the position of the white plate 53 and the projector-receiver 61 is normally separated approximately the distance s=0.5 mm to 3 mm from the back face 102b of original 102 in the original density measurement region.

After completion of calibration of the original density detecting apparatus, sheet feed rollers 103, 104 and sheet feed belt 105 shown in FIG. 1 are then rotated in the direction of the arrow A in the drawing to separate only the uppermost one of originals 102 mounted in the stack on the original tray 101 by cooperation with a stop roller 106 for preventing multiple feed and then convey it to the left on the drawing. At the same time, original conveying roller 121 and original conveying belt 107 start rotating to carry the original 102 to the left end of the original conveying belt 107 on the drawing.

The original 102 thus carried is then fed onto an original glass plate 114 by such a length that the leading end of the original 102 comes to the position of an image reading end 110 of the main body, by the original conveying belt 107 and press rollers 108, 109 rotating as following the motion thereof. At this time the original 102 passes near the original density detecting apparatus 200.

Thus, in FIG. 2, the light source (projector) 51 for detection of original density is turned on to emit light beams a to the surface 102a of original 102, and the photoelectric sensor (receiver) 55 receives the light reflected by the surface 102a of original 102 and the light after transmitted by the original 102, then reflected by the white plate 53 and again transmitted by the original 102 through the imaging lens 54. Then the sensor obtains an electric signal value v2 proportional to a quantity of the light received thereby. The reflectivity (reflection density) of the original 102 is calculated from the following calculation equation (1), using the electric signal value v1 resulting from the reflected light from the white plate 53 (the reflected light from the white plate 53 without original 102) as described above, the electric signal value resulting from the reflected light from the original 102 (the value proportional to the reflected light) v2, and the reflectivity of the white plate.

$$\text{Reflectivity of original} = \{\text{quantity of reflected light from original}/ \\ (\text{quantity of reflected light from white plate/reflectivity of} \\ \text{white plate})\} \quad (1)$$

In above Eq. (1), the quantity of the reflected light from the original 102 is the value of v2, i.e., the sum of a quantity of reflected light by the surface of original 102 and a quantity of the light transmitted by the original 102, then reflected by the white plate 53, and again transmitted by the original 102. Further, the quantity of the reflected light by the white plate 53 is a value of v1, i.e., a quantity of the light reflected by the white plate 53 without original 102.

Accordingly, above Eq. (1) is modified as follows.

$$\text{Reflectivity of original} = (v2/v1) \cdot (\text{reflectivity of white plate}) = (v2/ \\ v1) \cdot \{v1/(\text{quantity of light emitted from light source } 51)\} = v2/ \\ (\text{quantity of light emitted from light source } 51) \quad (1)'$$

Further, when the leading end of the original 102 comes to the image reading end 110 in FIG. 2, the movement of the original 102 is also stopped with stop of rotation of the original conveying belt 107. After the original 102 is located on the original glass plate 114 as pressed under appropriate pressure by rollers 111-1, 111-2, 111-3 disposed on the back of the original conveying belt 107, the copier main body 120 starts reading image information on the original 102 by an image reading optical system 130, thereby forming a latent image on a photosensitive drum 140. The image of the original 102 illuminated by a lamp 115 for illumination of original is formed on the photosensitive drum 140 by the image reading optical system 130 including a projection lens. The latent image is transferred onto a recording sheet by a well-known method.

Then a lighting voltage of the lamp (light source) 115 for illumination of original is set so as to make a copy in a density suitable for the reflectivity of original (reflection density) as described above and then exposure is started. After completion of exposure, the original conveying belt 107 and discharge roller 112 are again rotated to discharge the original 102 after reading of image information onto an original discharge tray 122.

By employing the method for measuring the density of original with respect to the reference of the white plate 53 having the reflectivity preliminarily known, as described above, the density of original can be detected accurately even with changes in the quantity of light emitted from the light source (LED) 51 due to deterioration thereof.

The copier having the automatic original supplying apparatus provided with the conventional original density detecting apparatus as described above has various problems described below.

The light a illuminating the original (conveyed original) 102, i.e., sheet 102 is scattered and diffused by fibers of the sheet 102 to be separated into components reflected by the surface 102a of the sheet 102 (reflected light) and components transmitted thereby (transmitted light).

Part of the light reflected by the surface 102a of the sheet (hereinafter referred to as "original") 102 decreases at a rate according to the reflectivity of the surface of the original 102 and travels toward the photoelectric sensor (receiver) 55. The transmitted light b illuminates the white plate 53 located at a position a little apart from the back face 102b of original 102. The light b illuminating this white plate 53 is reflected by the white plate 53. Part of the light b reflected by the white plate 53 is again incident to the back face 102b of original 102. Among the light incident to the back face 102b of the original 102, part is reflected and the other part is transmitted. The transmitted part of the light is incident through the imaging lens 54 to the photoelectric sensor 55 located on the side of surface 102a of original 102. The reflected part of the light again illuminates the white plate 53.

As described above, the light incident to the photoelectric sensor 55 includes the light reflected by the surface 102a of the original 102 and the light transmitted by the original 102, then illuminating the white plate 53 located on the side of back face 102b of the original 102, then reflected thereby, and again transmitted by the original 102. As the distance from the back face 102b of the original 102 to the surface 53a of the white plate 53 on the side of projector-receiver 61 becomes longer, the quantity of the reflected light from the white plate 53 decreases. As a result, the quantity of the light irradiating the photosensor 55 (the quantity of incident light thereto) decreases.

The thinner the original 102, the greater the transmittance of original and, on the contrary, the smaller the reflectivity of original.

Further, the white plate 53 upon detection of the reflectivity of original is normally positioned 0.5 or more mm apart from the back face 102b of original 102, as shown in FIG. 2. Because of it, the quantity of the light incident to the photoelectric sensor 55 becomes smaller than a quantity of reflected light when the original conveying belt 107 is in adhesion to the back face 102b of original 102 upon actual copying and, therefore, the reflectivity of original is determined to be lower.

As a result, control is made to increase the lighting voltage of the lamp (light source) 115 for illumination of original, illuminating the original 102, and thereby increase the quantity of the light illuminating the original 102. This results in a problem that the original 102 is copied under a higher quantity of illumination light than necessitated when the original 102 is conveyed to the copy position (or onto the original glass plate) by the original conveying belt 107.

FIG. 3 shows reflectivities of originals (reflection densities) (1) upon actual copying and reflectivities of originals (3) in the arrangement where the white plate 53 is positioned 0.5 mm apart from the back face 102b of original 102, with respect to changes in thickness of sheet.

In the drawing the ordinate represents measured values of reflectivity of original and the abscissa kinds of paper. The kinds of paper indicate differences of thickness. For example, 200 g sheet is thick, whereas 52 g sheet is thin. Sheets used are as follows: 200 g sheet (Japan) is Ginwa (silver ring) 200 g sheet available from CANON SALES CO., INC. (Canon Hanbai); 200 g sheet (US) is SPRING-HILL sheet; 80 g sheet is KANGAS sheet; 64 g sheet is PB sheet available from CANON INC.; 52 g sheet is Ginwa (silver ring) 52 g sheet available from CANON SALES CO., INC. (Canon Hanbai).

In the drawing the reflectivities of original are calculated based on foregoing Eq. (1). The reflectivity of each original (1) upon copying is given as follows.

Reflectivity of original (1) upon copy={(quantity of light reflected by surface of original 102)+(quantity of light transmitted by original 102, reflected by original conveying belt 107, and again transmitted by original 102)}/(quantity of light emitted from light source 115 upon copy)

In the drawing, curve (1) indicates measured values of reflectivity of originals upon actual copying where the conveying belt 107 is in adhesion with the back face 102b of original 102. Curve (3) indicates measured values of reflectivity of originals where the white plate 53 is positioned the distance s=0.5 mm apart from the back face 102b of the original 102. It is seen from this result of experiment that the reflectivities of originals with use of the white plate 53 (curve (3)) are largely different from the curve (1) of reflectivities of originals upon copying, depending upon the thickness of original 102.

It was thus difficult for the conventional original density detecting apparatus using the white plate to accurately detect a measured value of reflectivity of original (reflection density) for thinner originals or with longer distances between the back face of original and the white plate, as shown in FIG. 3. Curves (2) and (4) in FIG. 3 are measured values of reflectivity of originals of the present invention described hereinafter.

SUMMARY OF THE INVENTION

An object of the present invention is to provide an original density detecting apparatus in a simple structure capable of enhancing the detection accuracy of reflectivity of original (reflection density) regardless of the thickness of original by such an arrangement that a projector-receiver, in which a projector for illuminating an original (measured object) under conveyance and a receiver for receiving a beam (reflected beam and transmitted beam) from the original are placed in a same printed board, and a reflecting member (reference plate) as a reference of density of original are disposed with the original inbetween in an original density measurement region, that the reflecting member is a fluorescent reflecting plate with a coating of a fluorescent dye, and that the fluorescent reflecting plate is formed in an appropriate shape.

The original density detecting apparatus of the present invention is an original density detecting apparatus for detecting a density of an original using a projector-receiver and a reflecting member disposed with the original inbetween in a measurement region while the original is conveyed through the measurement region to a predetermined position by original conveying means, wherein the reflecting member comprises a fluorescent reflecting plate a surface of which on the projector-receiver side is a coating of a fluorescent dye.

Particularly, the apparatus is characterized in that a shape of the surface of the fluorescent reflecting plate on the projector-receiver side is convex;

in that the fluorescent dye comprises a fluorescent dye containing a main ingredient selected from diaminostilbene, uranin, thioflavine T, eosin, and rhodamine B; or in that the projector-receiver has a projector for illuminating the original under conveyance and a receiver for receiving a reflected beam from the original among beams from the projector and a beam transmitted by the original, then reflected by the fluorescent reflecting plate, and again transmitted by the original.

DETAILED DESCRIPTION OF THE PREFERRED EMBODIMENTS

Figure 4:
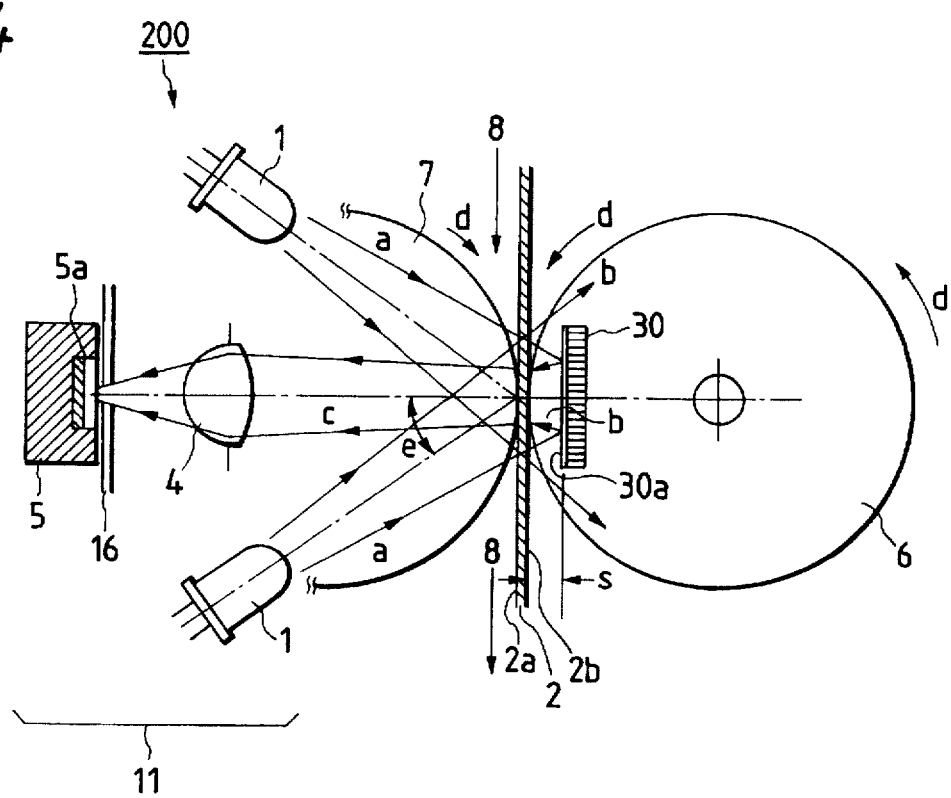
FIG. 4 is a schematic drawing of the major part of Embodiment 1 of the original density detecting apparatus according to the present invention.

FIG. 4 is a schematic drawing of the major part of Embodiment 1 of the original density detecting apparatus according to the present invention, which shows a mechanism for detecting the reflection density (reflectivity) of the original in the measurement region on the way of conveyance of original in the original conveyance path (sheet path section). Since the structure of the image forming apparatus to which the original density detecting apparatus of Embodiment 1 is applied is the same as in the conventional example, the description thereof is omitted herein.

In the drawing reference numeral 1 designates a light source as a projector (light projecting device) for detection of density of original, which is comprised of LEDs, for example, and which irradiates an original (conveyed original) 2 as a measured object passing in the original conveyance path 8, in the measurement region.

Numeral 5 denotes a photoelectric sensor (original density detection sensor) as a receiver (light receiving device) for detection of density of original, which is comprised of a photosensor or the like, for example, and which receives the reflected light from the original 2 illuminated by the beams from the light source 1 and the light transmitted by the original 2, then reflected by a fluorescent reflecting plate 30 as a reflecting member (reference plate) described hereinafter, and again transmitted by the original 2 through the imaging lens 4 to detect the reflection density (reflectivity) of the original 2. The projector 1 and receiver 5 are placed on a same printed board. The projector 1 and receiver 5 disposed on the printed board will be referred to together as projector-receiver 11.

Numeral 16 denotes a slit to limit a beam incident to the photoelectric sensor 5.

Numeral 30 represents a reflecting member (reference plate) used as a reference of density of original and having a reflectivity preliminarily known, which is a fluorescent reflecting plate a surface 30a of which on the projector-receiver 11 side is a coating of a fluorescent dye. The fluorescent dye used in this florescent reflecting plate 30 is a fluorescent dye in which diaminostilbene, uranin, thioflavine T, eosin, or rhodamine B is dissolved. An example of the fluorescent plate commercially available is Luminotape (registered trademark) #200 available from Sinroihi Kabushiki Kaisha.

The present embodiment uses the fluorescent reflecting plate 30 with the coating of the fluorescent dye as a reflecting means for detection of density of original as described below, whereby the reflectivity of original is increased from that upon use of the conventional white plate, thereby improving the detection accuracy of density of original.

The fluorescent reflecting plate 30 and the above projector-receiver 11 are positioned with the original 2 inbetween in the measurement region of the original conveyance path 8 and the fluorescent reflecting plate 30 is located approximately 0.5 mm apart from the back face 2b of original 2 in the measurement region.

Numerals 6, 7 are conveying rollers, each constituting an element of the original conveying means, which are positioned on either side of the original conveyance path 8. In the present embodiment the conveying rollers 6, 7 are arranged to convey the original 8 when rotated in the directions of arrows d shown in the drawing, and detection of reflection density of the original 2 is carried out at the same time as it.

The original feed operation, copy operation, and so on in the present embodiment are the same as in the conventional example described previously. Next described is the original density detecting method according to the present embodiment.

Calibration of the original density detecting apparatus is first carried out. In the present embodiment, the light source (LEDs) 1 as a projector emits the beams to the fluorescent reflecting plate 30 having the preliminarily known reflectivity, the photoelectric sensor (photosensor) 5 as a receiver receives the reflected light from the fluorescent reflecting plate 30 through the imaging lens 4, the photosensor converts the received light to an electric value (electric signal value) v1 proportional to a quantity of the received light by photoelectric conversion, and the electric value v1 is stored in a memory (not shown). The electric signal value v1 at this time is used as a reference of density of original.

After completion of calibration of the original density detecting apparatus, an original 2 mounted in the stack on the original tray (not shown) is conveyed through the original conveyance path 8 onto the original glass plate (not shown) and reading of image information on the original 2 is started. In the present embodiment, when the conveyed original 2 passes near the original density detecting apparatus at this time as shown in FIG. 4, the light source 1 is turned on to radiate the beams a to the surface 2a of original 2, and the beams are scattered and diffused by fibers of the original (sheet) 2 to be separated into components reflected by the surface 2a of the original 2 (reflected light) and components transmitted thereby (transmitted light).

Part of the reflected light by the surface 2a of original 2 decreases at a rate according to the reflectivity of the surface of the original 2 and travels toward the photoelectric sensor (receiver) 5. Further, the transmitted light b irradiates the fluorescent reflecting plate 30 located at a position a little apart from the back face 2b of the original 2. The light b irradiating the fluorescent reflecting plate 30 is reflected by the fluorescent reflecting plate 30. Then part of the light b reflected by the fluorescent reflecting plate 30 is again incident to the back face 2b of original 2. Among the light incident to the back face 2b of the original 2, part is reflected and the other part is transmitted. Part of the transmitted light is incident through the imaging lens 4 to the photoelectric sensor 5 placed on the side of surface 2a of original 2. Further, part of reflected light again irradiates the fluorescent reflecting plate 30.

As described above, the light incident to the photoelectric sensor 5 includes the light reflected by the surface 2a of original 2 and the light transmitted by the original 2, then irradiating the fluorescent reflecting plate 30 located on the side of back face 2b of the original 2, reflected thereby, and again transmitted by the original 2.

Then obtained is an electric signal value (a value proportional to the reflected light) v2 proportional to the quantity of the light incident to the photoelectric sensor 5. Then the reflectivity (reflection density) of the original 2 is calculated by arithmetic equation (1) described previously from the ratio of the electric signal value v2 and the electric signal value v1 resulting from the reflected light from the fluorescent reflecting plate 30, obtained upon the calibration as discussed above. The point is that for calculation of the present embodiment, the fluorescent reflecting plate replaces the conventional white plate.

Figure 1:
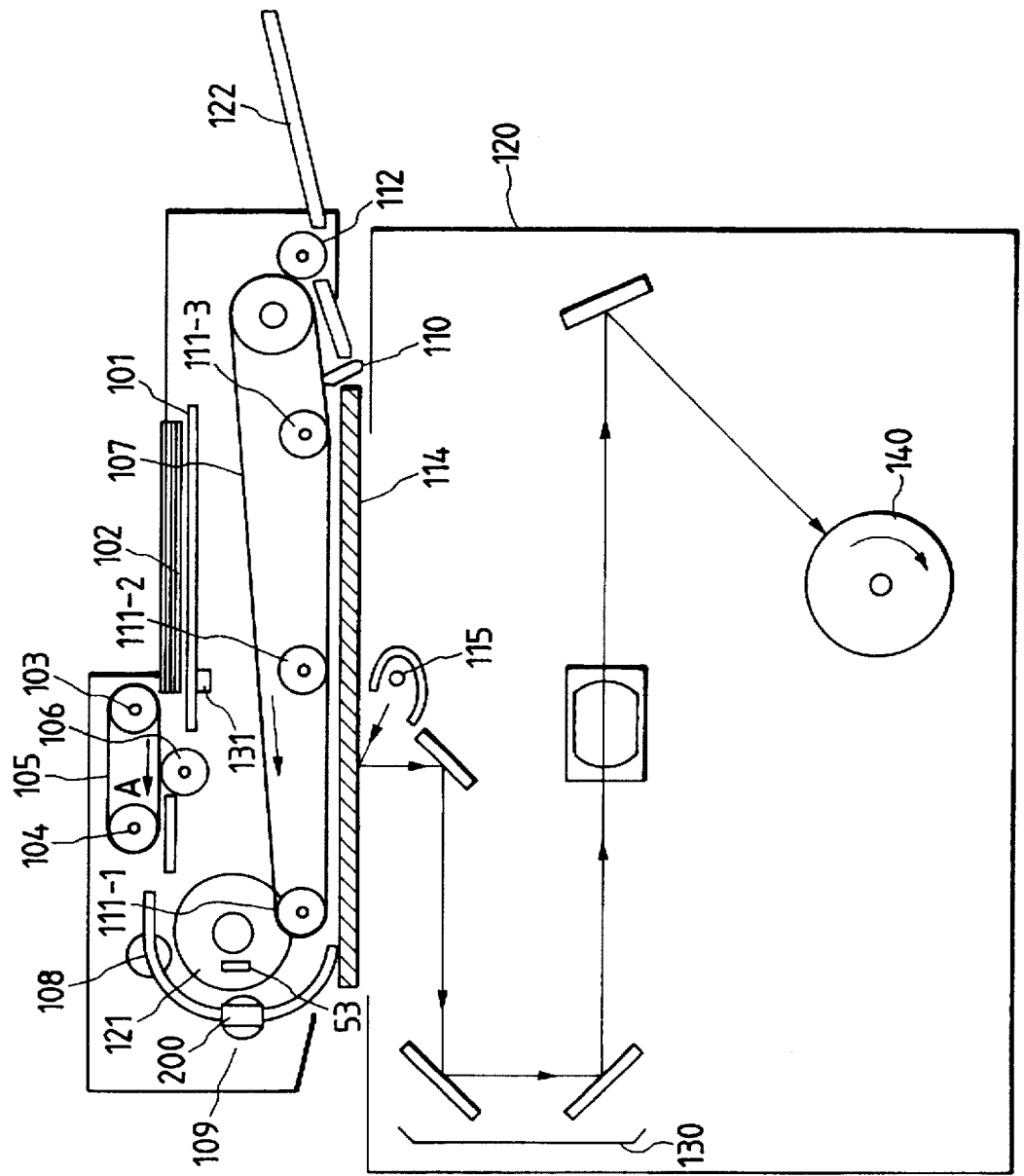
FIG. 1 is a schematic drawing of the major part of the conventional copier provided with the original supplying apparatus.
Figure 2:
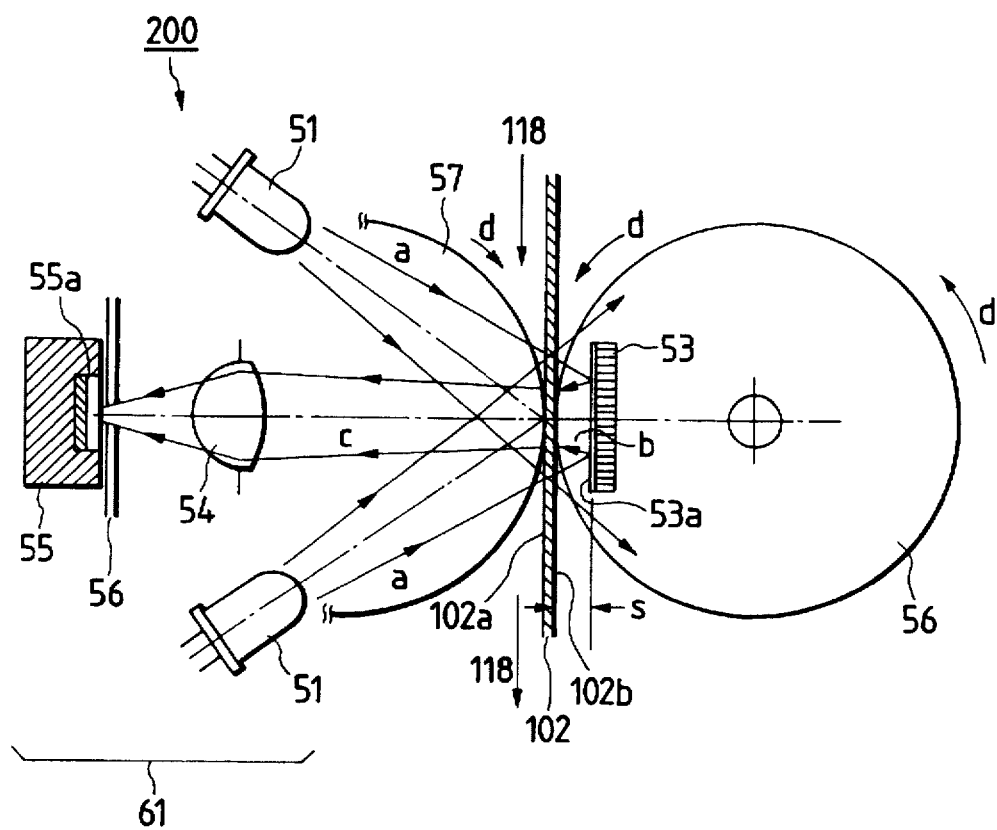
FIG. 2 is a schematic drawing of the major part of the conventional original density detecting apparatus.
Figure 3:
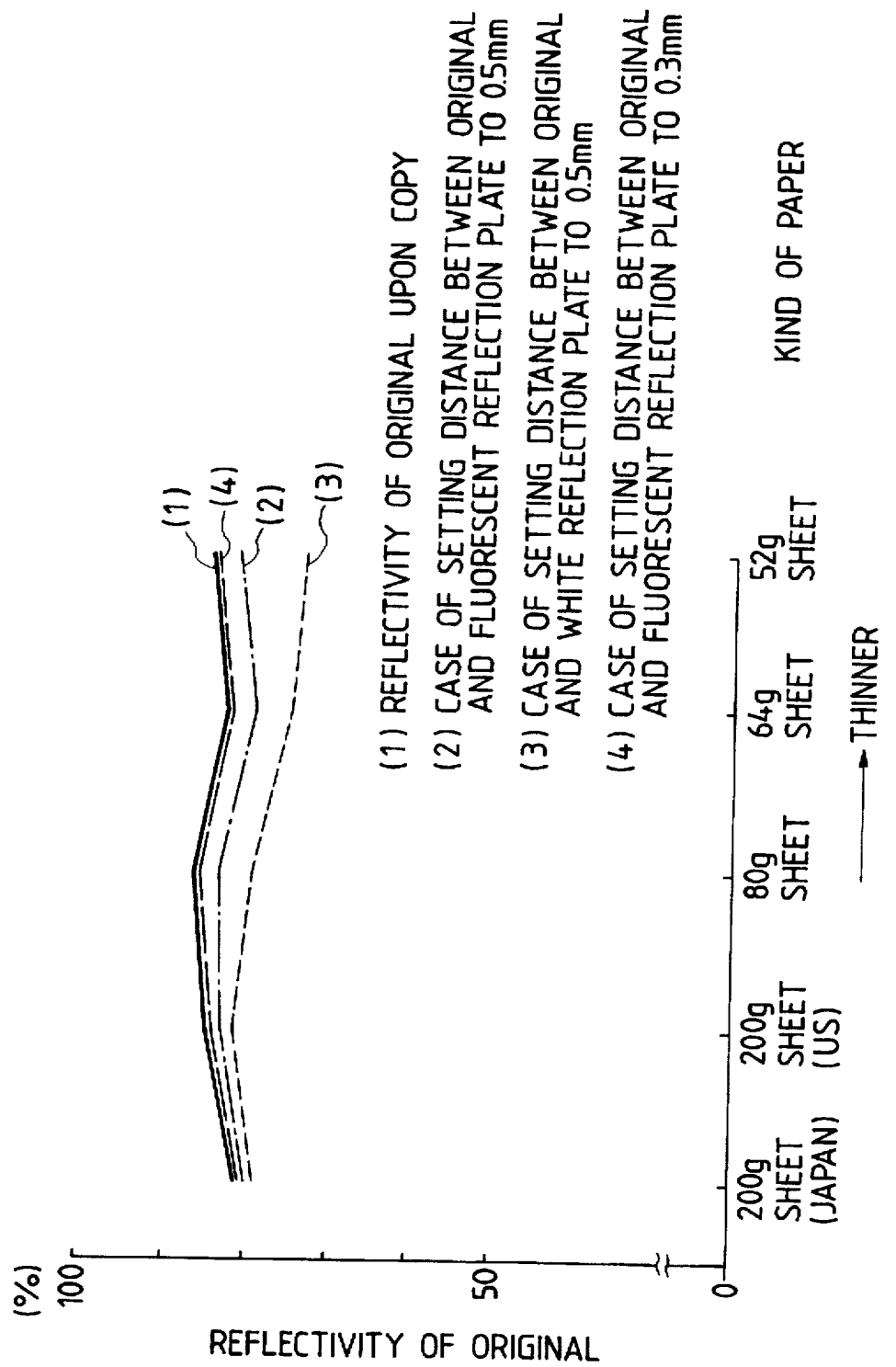
FIG. 3 is an explanatory drawing to show measured values of reflectivity of original in Embodiments 1, 2 and the conventional example.

Measured values of reflectivity of the originals having various thicknesses are shown by curve (2) in FIG. 3. Curve (2) indicates the measured values of reflectivity of the originals by the present embodiment where the fluorescent surface 30a of the fluorescent reflecting plate 30 on the projector-receiver 11 side is located about the distance s=0.5 mm apart from the back face 2b of original 2. It is seen from the drawing that differences of the measured values from those on curve (1) indicating the measured values of reflectivity of the originals upon copying are smaller than those between curve (1) and curve (3) indicating the measured values of reflectivity of the originals by the conventional white plate.

As described above, the present embodiment is arranged to detect the reflection density (reflectivity) of the original 2 using the projector-receiver 11 and fluorescent reflecting plate 30 disposed with the original inbetween in the measurement region of the original conveyance path 8 in the above manner, whereby, for example with thin originals 2, the light reflected by the surface 2a of the original 2 and the light transmitted by the original 2, then reflected by the fluorescent reflecting plate 30, and again transmitted by the original 2 is efficiently incident to the photoelectric sensor (receiver) 5, which can avoid an extreme reduction in light quantity when compared with the conventional original density detecting apparatus using the white plate and which can permit appropriate detection of reflectivity of original 2. Further, with thick originals 2, influence of thickness is small because of a small decrease from the original reflectivity and transmitted light by the original 2 is little, so that the reflected light from the fluorescent reflecting plate 30 rarely returns to the photoelectric sensor (receiver) 5. Therefore, the detection accuracy of accurate reflectivity of original 2 can be assured.

Figure 5:
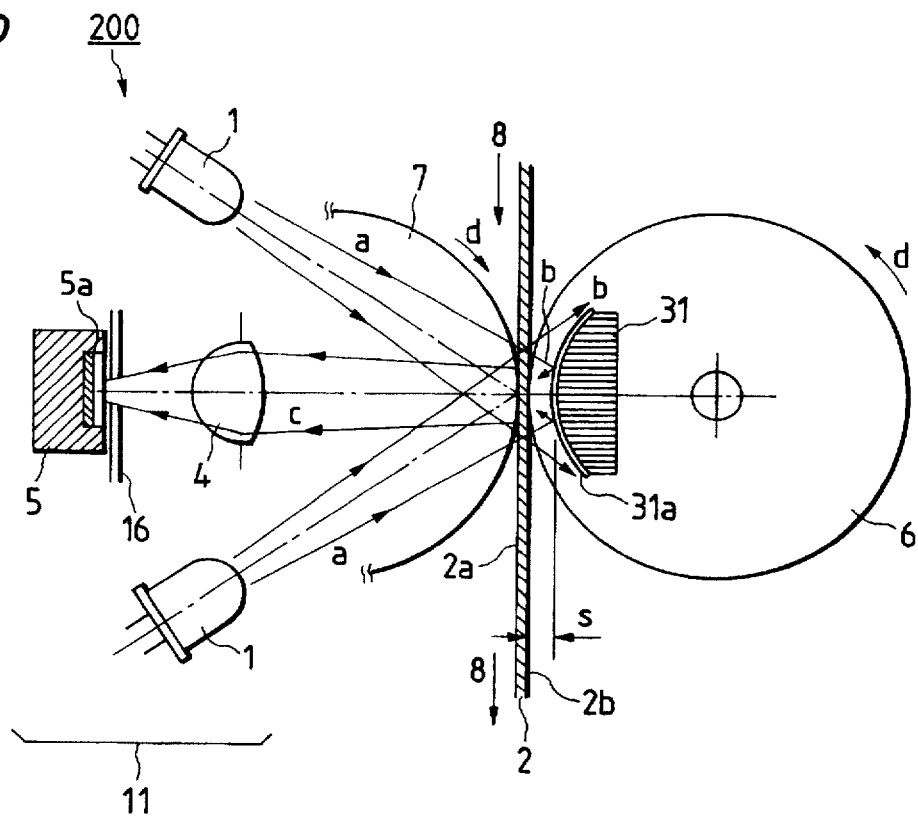
FIG. 5 is a schematic drawing of the major part of Embodiment 2 of the original density detecting apparatus according to the present invention.

FIG. 5 is a schematic drawing of the major part of Embodiment 2 of the original density detecting apparatus according to the present invention, which shows a mechanism for performing detection of the reflection density (reflectivity) of the original in the measurement region on the way of conveyance of original in the original conveyance path (sheet path section). In the drawing the same elements as those shown in FIG. 4 are denoted by the same reference numerals. Since the structure of the image forming apparatus to which the original density detecting apparatus of Embodiment 2 is applied is the same as in the conventional example, the description thereof is omitted herein.

The present embodiment is different from foregoing Embodiment 1 in that the surface of the fluorescent reflecting plate 31 on the projector-receiver 11 side is formed in a convex shape (or in a shape of a convex mirror). The other structure and optical action is substantially the same as those in Embodiment 1, thereby achieving the same effects.

In the drawing, reference numeral 31 denotes a fluorescent reflecting plate as a reflecting member (reference plate), which is formed in such a configuration that the shape of the surface of the fluorescent reflecting plate 31 on the projector-receiver 11 side is a convex shape (a shape of a convex mirror), that a nearly central portion of the fluorescent reflecting plate 31 projects toward the back face 2b of original 2 further from that in foregoing Embodiment 1, and that ends of the fluorescent reflecting plate 31 are placed more distant from the original 2 than the central portion is. When the fluorescent reflecting plate 31 is shaped as described and if the fluorescent reflecting plate 31 should touch the conveyed original 2, the fluorescent surface 31a would be shaved. Therefore, the present embodiment is arranged so that the distance s from the back face 2b of original 2 to the fluorescent surface 31a of the central portion of the fluorescent reflecting plate 31 is s=0.3 mm approximately.

Measured values of reflectivity of the originals having the various thicknesses are shown by curve (4) in FIG. 3. Curve (4) indicates the measured values of reflectivity of the originals according to the present embodiment where the fluorescent surface 31a of the central portion of the fluorescent reflecting plate 31 is located about the distance s=0.3 mm apart from the back face 2b of the original 2. It is seen from the drawing that differences of the measured values of curve (4) from curve (1) indicating the measured values of reflectivity of the originals upon copying become further smaller than those of curve (2) indicating the measured values of reflectivity of the originals in foregoing Embodiment 1.

The present invention can achieve the original density detecting apparatus in the simple structure capable of enhancing the detection accuracy of reflectivity (reflection density) of original regardless of the thickness of original (measured object) by the arrangement wherein the projector-receiver having the projector and the receiver and the reflecting member (reference plate) as a reference of density of original are disposed with the original (measured object) inbetween in the original density measurement region and wherein the reflecting member is the fluorescent reflecting plate with the coating of the fluorescent dye as described above.

In addition, the present invention can achieve the original density detecting apparatus in the simple structure capable of further enhancing the detection accuracy of reflectivity (reflection density) of original by the arrangement wherein the surface of the fluorescent reflecting plate on the projector-receiver side is formed in the convex shape (in the shape of a convex mirror) as described above, whereby the ends of the fluorescent reflecting plate, easily catching the original, can be placed more distant from the conveyed original so as to avoid contact with the conveyed original and to be prevented from impeding conveyance of original and whereby the center portion can be set closer to the original surface than the end portions, thereby further increasing the reflected light from the fluorescent reflecting plate.

When the original density detecting apparatus of the present invention is applied to the image forming apparatus, the reflectivity of original can be detected accurately and an excellent image can be formed on the photosensitive drum.

What is claimed is:

1. An original density detecting apparatus comprising:
   a projector-receiver comprising a light projector and a light receiver; and
   a reflecting member comprising a fluorescent reflecting plate, wherein a surface of said fluorescent reflecting plate which faces said projector-receiver has a coating of a fluorescent dye.

2. The original density detecting apparatus according to claim 1, wherein said light projector illuminates an original and wherein said light receiver receives a beam of reflected light from said original and a beam of light transmitted by said original, then reflected by said fluorescent reflecting plate, and again transmitted by said original.

3. The original density detecting apparatus according to claim 1, wherein said fluorescent reflecting plate has a convex surface which faces said projector-receiver.

4. The original density detecting apparatus according to claim 1, wherein said fluorescent dye is a fluorescent dye containing a main ingredient selected from the group consisting of diaminostilbene, uranin, thioflavine T, eosin, and rhodamine B.

5. The original density detecting apparatus according to claim 1, which is used for detection of a reflection density of an original in an image forming apparatus.

6. An image forming apparatus comprising:
   illuminating means for illuminating an original;
   image reading means for forming an image of said original on a photosensitive medium; and
   an original density detecting apparatus for detecting a reflection density of said original, said original density detecting apparatus comprising a projector-receiver comprising a light projector and a light receiver, and a reflecting member comprising a fluorescent reflecting plate, wherein a surface of said fluorescent reflecting plate which faces said projector-receiver has a coating of a fluorescent dye.

7. The image forming apparatus according to claim 6, wherein said light projector illuminates the original and wherein said light receiver receives a beam of reflected light from said original and a beam of light transmitted by said original, then reflected by said fluorescent reflecting plate, and again transmitted by said original.

8. The image forming apparatus according to claim 6, wherein said fluorescent reflecting plate has a convex surface which faces said projector-receiver.

9. The image forming apparatus according to claim 6, wherein said fluorescent dye is a fluorescent dye containing a main ingredient selected from the group consisting of diaminostilbene, uranin, thioflavine T, eosin, and rhodamine B.

* * * * *